United States Patent
Barger et al.

(10) Patent No.: US 9,296,658 B2
(45) Date of Patent: Mar. 29, 2016

(54) GYPSUM MANUFACTURING PROCESS IMPROVEMENT

(71) Applicant: Georgia-Pacific Gypsum LLC, Atlanta, GA (US)

(72) Inventors: William E. Barger, Heber City, UT (US); Carmine Perri, Atlanta, GA (US)

(73) Assignee: Georgia-Pacific Gypsum LLC, Atlanta, GA (US)

( * ) Notice: Subject to any disclaimer, the term of this patent is extended or adjusted under 35 U.S.C. 154(b) by 208 days.

(21) Appl. No.: 13/944,930

(22) Filed: Jul. 18, 2013

(65) Prior Publication Data

US 2014/0020603 A1  Jan. 23, 2014

Related U.S. Application Data

(60) Provisional application No. 61/673,527, filed on Jul. 19, 2012.

(51) Int. Cl.
*C04B 28/14* (2006.01)
*G01N 23/222* (2006.01)
*C04B 40/00* (2006.01)

(52) U.S. Cl.
CPC ............. *C04B 28/14* (2013.01); *C04B 40/0032* (2013.01); *G01N 23/222* (2013.01)

(58) Field of Classification Search
CPC .. C04B 28/14; C04B 41/0032; G01N 23/223; B28C 7/00; B28C 7/02; B28C 7/024
See application file for complete search history.

(56) References Cited

U.S. PATENT DOCUMENTS

| | | | |
|---|---|---|---|
| 4,026,717 A | 5/1977 | Harris et al. | |
| 4,882,927 A * | 11/1989 | Gould | ............................ 73/1.01 |
| 7,663,108 B2 | 2/2010 | Mound et al. | |
| 2004/0095571 A1 * | 5/2004 | Bourely et al. | ............ 356/237.1 |
| 2007/0263212 A1 | 11/2007 | Mound | |
| 2010/0082157 A1 | 4/2010 | McGarel et al. | |

FOREIGN PATENT DOCUMENTS

WO  99/08978 A1  2/1999

OTHER PUBLICATIONS

International Search Report and Written Report for International Application No. PCT/US2013/051054 mailed Oct. 1, 2013.

* cited by examiner

*Primary Examiner* — Yara B Green
(74) *Attorney, Agent, or Firm* — Ram W. Sabnis

(57) ABSTRACT

The present application provides a method for analyzing a raw material for manufacturing of gypsum products, analyzing a plurality of gypsum products, and the gypsum products produced therefrom. Desirably, the analyzing of the raw material is conducted using prompt gamma neutron activation analysis.

17 Claims, 4 Drawing Sheets

GYPSUM MANUFACTURING PROCESS IMPROVEMENT

CROSS-REFERENCE TO RELATED APPLICATIONS

This application claims priority to U.S. Provisional Patent Application having Ser. No. 61/673,527, filed on Jul. 19, 2012, which is incorporated by reference herein.

BACKGROUND OF THE INVENTION

The present application relates generally to improved gypsum products and their methods of manufacture. More particularly, it relates to use of elemental detection in gypsum manufacturing processes.

Gypsum boards have been used extensively in the construction of both residential and commercial buildings. A typical gypsum board comprises a gypsum core disposed between two sheets of a paper (e.g., multi-ply paper), fiber glass mat, or cardboard material, known as facing layers. The conventional manufacturing of gypsum board for use in wall and roofing materials is well known and generally involves forming a core layer of wet slurry between the two layers of facing materials. When the wet core sets and is dried, a strong, rigid, and fire-resistant building material results.

The increasing production and quality demands in gypsum manufacturing processes, particularly gypsum wallboard processes, have resulted in a need for improvements to the speed and accuracy of quality control processes. Existing quality control processes rely on extractive sampling from gypsum slurry. These samples then are transported to a separate laboratory for further analysis. By the time the results are received, however, the production run has long-since been completed. Historically, engineers have overcome these deficiencies by manually controlling the rates of raw feed materials based to produce a product having the desired physical properties. Thus, there remains a perceived need in the art for improved methods for the manufacture of gypsum wallboard, particularly methods that will improved the quality and consistency of gypsum wallboard.

SUMMARY OF THE INVENTION

Embodiments of the present application include methods for analyzing a raw material for manufacturing a plurality of gypsum products. Generally described, the method comprises analyzing the raw material using an elemental analyzer; detecting and/or measuring an amount of one or more target chemicals in the raw material; and optimizing the amount of the one or more target chemicals in the raw material to improve consistency and quality of the plurality of gypsum products manufactured from the raw material. Desirably, the step of analyzing the first raw material feed stream comprises using an online elemental analyzer.

Embodiments of the present application also include methods for analyzing a plurality of gypsum products. Generally described, the method comprises analyzing the plurality of gypsum products using an elemental analyzer comprising a prompt gamma neutron activation analysis; detecting and/or measuring the quality of the plurality of gypsum products; and sorting the plurality of gypsum products based on the quality to improve consistency and quality of the plurality of gypsum products.

Still other embodiments of the present application include methods for analyzing and sorting a raw material for manufacturing a plurality of gypsum products on site at a mine. The method comprises analyzing the raw material on site at a mine using an elemental analyzer comprising a prompt gamma neutron activation analysis; detecting and/or measuring an amount of one or more target chemicals in the raw material; and sorting the raw material according to the presence of and/or amount of one or more target chemicals in the raw material.

These and other features and improvements of the present application and the resultant patent will become apparent to one of ordinary skill in the art upon review of the following detailed description when taken in conjunction with the several drawings and the appended claims.

DETAILED DESCRIPTION OF THE INVENTION

The present application addresses the above-described needs by providing a process for manufacturing gypsum products using real time process control.

Figure 4:
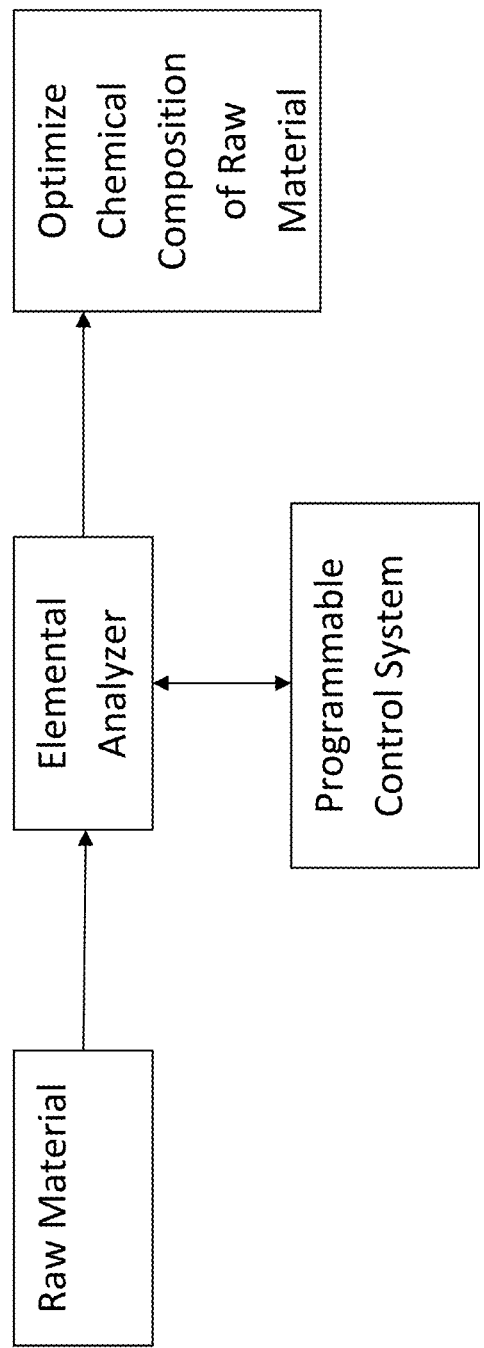
FIG. 4 is a schematic illustration of a method for analyzing a raw material for manufacturing a plurality of gypsum products.

Generally described, and illustrated in FIG. 4, embodiments of the method for analyzing a raw material for manufacturing of gypsum products comprises analyzing the raw material using an elemental analyzer; detecting and/or measuring an amount of one or more target chemicals in the raw material; and optimizing the amount of the one or more target chemicals in the raw material to improve consistency and quality of the plurality of gypsum products manufactured from the raw material.

In embodiments, the method further comprises the step of sorting the raw material according to the presence and/or amount of the one or more target chemicals in the raw material.

In embodiments, the step of optimizing the amount of the one or more target chemicals in the raw material comprises mixing the raw material one or more of a plurality of other materials in appropriate proportions to produce a raw material having a specified chemical composition.

As used herein, improved consistency and quality may be measured relative to a gypsum product manufactured without the use of elemental analysis. In embodiments, the improved consistency and quality is characterized by a plurality of gypsum products having reduced weight variability, an improved content uniformity, or a combination thereof. For example, a plurality of gypsum products may be characterized as having a reduced weight variability when the weight variability of the plurality of gypsum products is less than about 150 lbs per 1000 ft$^2$, less than about 100 lbs per 1000 ft$^2$, less than about 50 lbs per 1000 ft$^2$, or less than about 10 lbs per 1000 ft$^2$. A plurality of gypsum products may be characterized as having an improved content uniformity when the variability of concentration of a target chemical in a plurality of gypsum products is less than about ±10%, less than about ±5%, less than about ±2%, or less than about ±1%.

Figure 1:
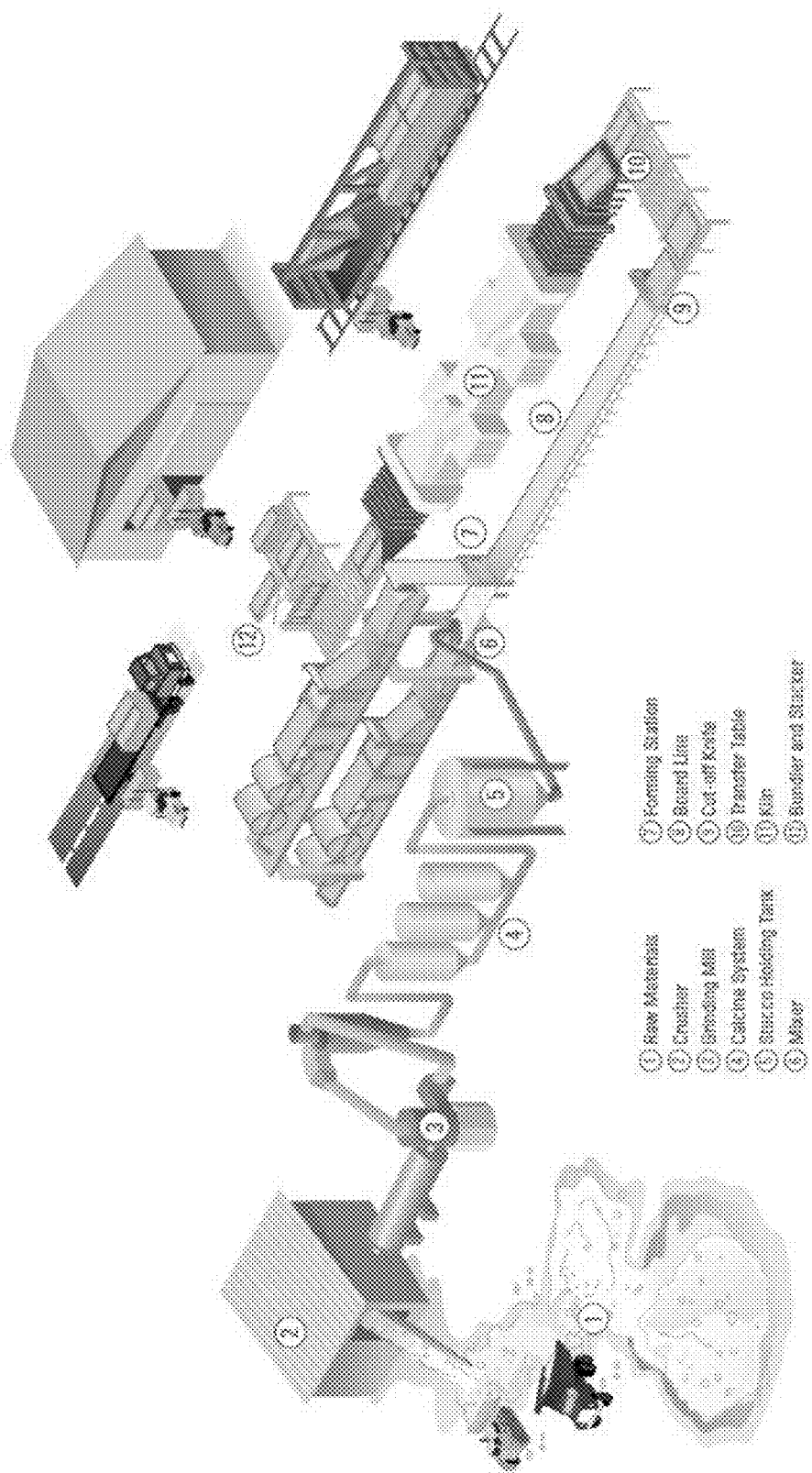
FIG. 1 is a schematic diagram of a gypsum board manufacturing process.

Referring now to the drawings, in which like numerals refer to like elements throughout the several views, FIG. 1 shows a general schematic diagram of a process for manufacturing gypsum board. The process generally includes extracting gypsum rock at mines or quarries (1), crushing the rocks into small pieces (2), grinding the small rocks to produce a very fine, chalk-like powder (called land plaster) (3), and heating the land plaster to remove most of the water from the plaster to produce a calcined land plaster (called stucco) (4). The stucco and any other optional dry components are pre-mixed and then fed to a mixer. Water and other liquid constituents (e.g., soap or foam, used to control the slurry density), used in forming the slurry, are metered into the mixer where they are combined with the dry components to form an aqueous gypsum slurry, which emerges from a discharge conduit of the mixer (6).

The slurry is deposited onto a continuous, horizontally moving lower facing sheet (7). The amount of slurry deposited can be controlled in manners known in the art. The lower facing sheet is fed from a roll. Prior to receiving the gypsum slurry, the lower facing sheet edges are folded upward. These edges can then be glued to overlapping portions of an applied immediately over the gypsum slurry according to methods known in the art.

The board travels down a conveyor line in a single continuous piece, during which the water rehydrates the stucco, causing it to harden (8). At the end of the line, a blade cuts the hardened board into various lengths (9), the cut lengths can be turned face-side up to protect the face paper or mat (10), and then fed into a kiln to complete the drying process. The gypsum board (11) then may be bundled to protect the face of the board, stacked, and transferred to the warehouse for shipping to customers (12).

Although embodiments of the methods of analyzing a raw material for manufacturing gypsum products provided herein are especially effective for use in the manufacture of gypsum boards, those skilled in the art should appreciate that the methods also may be used in manufacturing of other types of gypsum products, including plaster and joint compound.

Embodiments of the present description improve upon the above-described process by providing for the analysis of the raw material and a programmable control system to optimize the composition of the raw material. The method of analyzing the raw material may be conducted on site at a mine from which the raw materials are obtained or at any suitable point during the manufacturing of the gypsum products. For example, in an embodiment the raw material is analyzed on site at the mine, after crushing and/or grinding the raw material, before or after calcinating the raw material, before or after before or after forming a gypsum slurry, or before or after depositing the gypsum slurry on the facing sheet.

Figure 2:
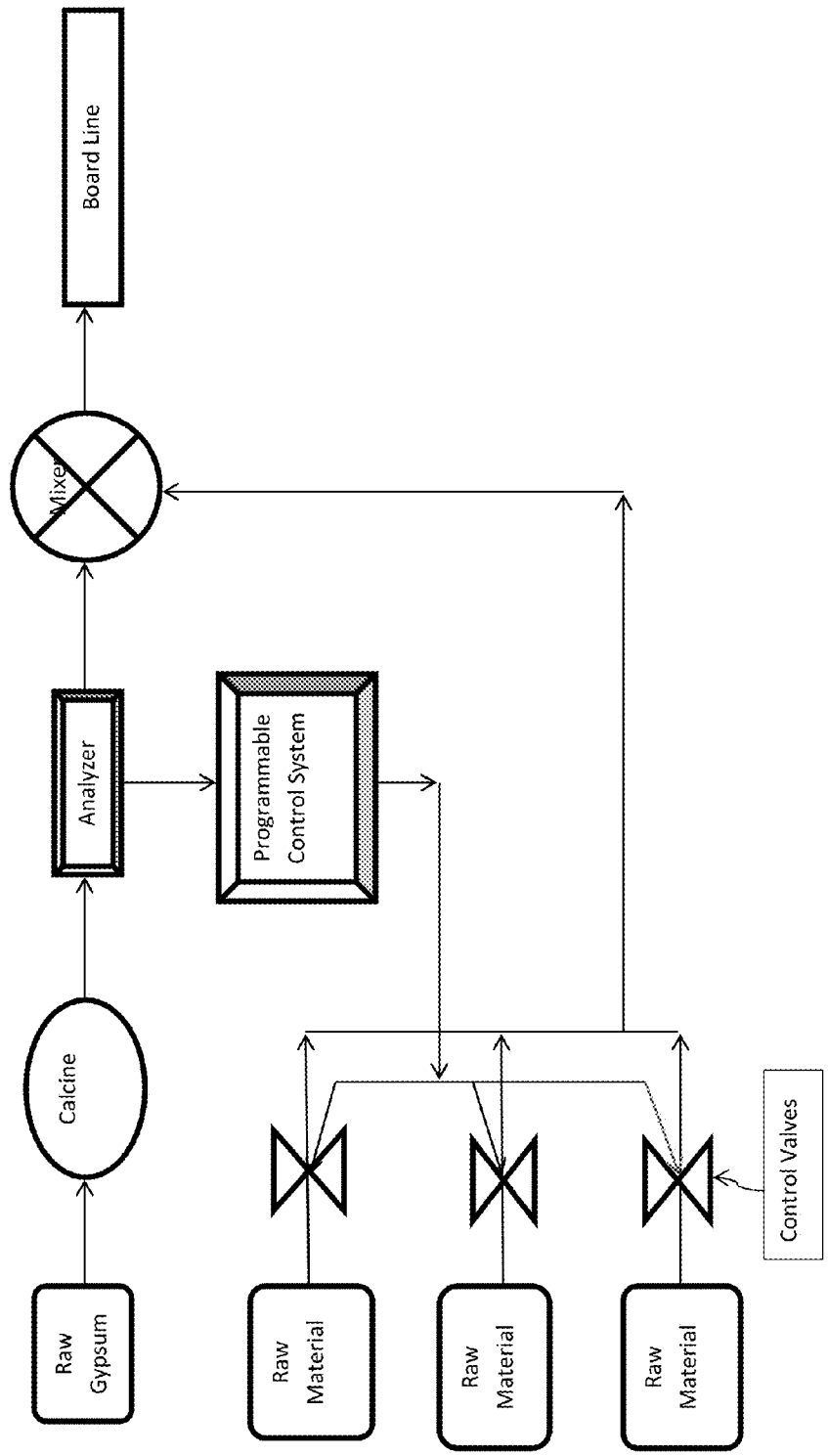
FIG. 2 is a schematic illustration of a gypsum board manufacturing process comprising a programmable control system according to an embodiment.
Figure 3:
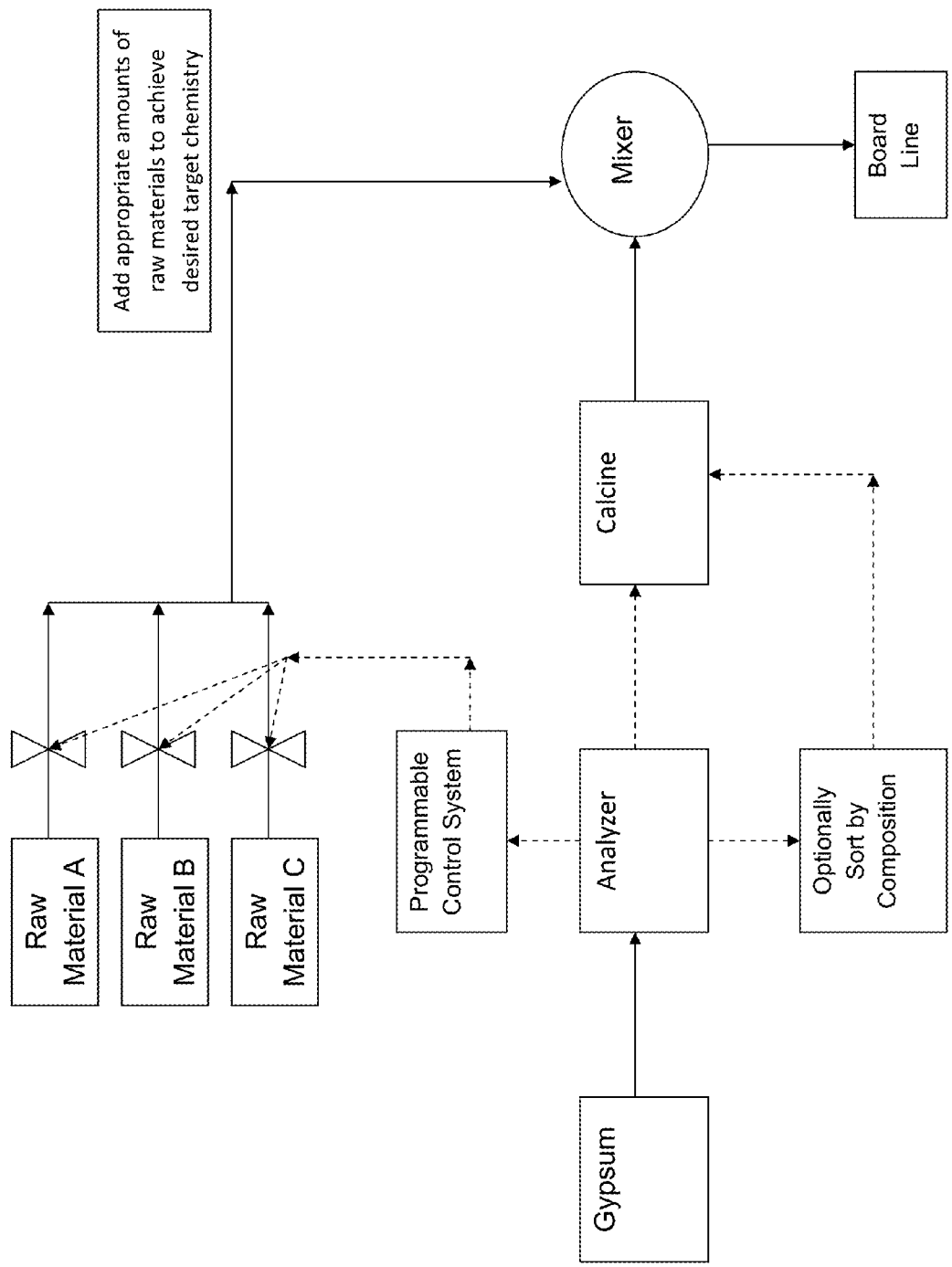
FIG. 3 is a schematic illustration of a gypsum board manufacturing process comprising a programmable control system according to an embodiment.

Exemplary embodiments of a method for analyzing a raw material during the manufacturing of a plurality of gypsum products are illustrated in FIGS. 2 and 3, in which a plurality of raw material feed streams are provided, at least one of the raw material feed streams comprising gypsum. The raw material may be analyzed online to determine the actual composition of the material feed at any suitable point in the process.

Any elemental analyzer that may be configured to measure and/or detect and determine the actual composition of the raw material feed may be used, non-limiting examples of which include prompt gamma neutron activation analysis (PG-NAA), controlled neutron analysis, x-ray fluorescence, laser spectrometry, or x-ray diffraction. In an embodiment, the online analyzer comprises PGNAA (such systems are available, for example, from Thermo Scientific). The elemental analyzer may be used in combination with other sensors (i.e., measurement devices, transducers, and the like) coupled to one or more programmable controllers.

In embodiments, the elemental analyzer is configured to measure and/or detect an amount of one or more chemicals and minerals. For example, the elemental analyzer may be configured to measure and/or detect materials selected from the group consisting of gypsum (calcium sulfate dihydrate), calcium sulfate hemihydrate, calcium sulfate anhydrite, acid solubles, acid insolubles, organics, water, salt (e.g., chloride salts), sulfurs, aluminum silicates, calcium carbonate, and combinations thereof. Non-limiting examples of acid solubles include limestone, sand, shale, clay, silica phyllosilicates, or combinations thereof.

A programmable control system then may be used to optimize the amount of the one or more target materials in the raw material. For example, the programmable control system may be configured to calculate and control the proportioning of a raw material feed (i.e., using pumps, valves, and the like) based on the desired target composition of the gypsum product or to calculate and sort the raw material feed (i.e., using gates and valves and the like) based on the presence and/or absence of one or more target chemicals in the raw material.

In one embodiment, optimizing the amount of the one or more target chemicals in the raw material comprises mixing the raw material with one or more other materials to obtain a modified raw material having a specified chemical composition. For example, the programmable control system may meter the addition and amount of one or more of the plurality of other materials added to the raw material in a mixer to produce the modified raw material. Non-limiting examples of the one or more of the plurality of other materials include starch, potash, boric acid, accelerators, foaming agents, retarders, dispersing agents, and combinations thereof. Although FIG. 2 illustrates adding the other materials to the raw material in the mixer, those of ordinary skill in the art should appreciate that the raw materials and one or more of the plurality of other materials may be combined at any suitable point in the process downstream of the elemental analyzer. For example, the one or more of the plurality of other materials may be added to the raw material before or after calcinating the raw material.

In another embodiment, optimizing the amount of the one or more target chemicals in the raw material comprises sorting the raw material according to the presence of and/or amount of the one or more target chemicals in the raw material. For example, the programmable control system may detect and/or measure the amount of one or more target chemicals in the raw material and divert the raw material using a series of gates based on the presence and/or amount of the one or more target chemicals. By sorting the raw material at the mine or during the process of manufacturing the gypsum products, the composition of the resulting gypsum products can be better controlled. For example, in an embodiment the raw material may be sorted into a plurality of raw material feed streams, each having a respective concentration of calcium sulfate dihydrate. The raw materials feed streams then may be combined in desired proportions to obtain a raw material having the specified chemical composition (i.e., by combining a first raw material having a first concentration of calcium sulfate dihydrate concentration and a second raw material having a second calcium sulfate dihydrate concentration to obtain a raw material having a specified concentration of calcium sulfate dihydrate).

In still another aspect, a plurality of analyzed gypsum products are provided. The plurality of analyzed gypsum products have improved consistency as characterized by a reduced weight variability, an improved content uniformity, or a combination thereof. In one aspect, the plurality of analyzed gypsum products may be produced using the raw materials analyzed using the methods described in embodiments hereinabove. In another aspect, the plurality of gypsum analyzed products may be analyzed by a method comprising analyzing the plurality of gypsum products using an elemental analyzer (i.e., a prompt gamma neutron activation analysis), detecting and/or measuring the consistency and quality of the plurality of gypsum products; and sorting the plurality of gypsum products based on the consistency and quality of the gypsum products to improve the consistency and quality of the plurality of gypsum products. As discussed hereinabove, the improved consistency and quality of the plurality of gypsum products desirably are characterized as having an improved content uniformity and a reduced weight variability.

Embodiments of the claimed methods improve upon the existing gypsum manufacturing processes by providing real time process control capabilities, significantly reducing the time currently required to analyze samples from the gypsum slurry, and improving product quality and consistency.

EXAMPLES

Exemplary Example 1

An exemplary embodiment of a method for analyzing a raw material for the manufacture of gypsum products is illustrated in FIG. 2. A raw material comprising gypsum is provided and is calcined prior to undergoing elemental analysis. The elemental analyzer is configured to detect and measure the concentration of one or more target chemicals, for example, calcium sulfate dehydrate, in the calcinated raw material. A programmable control system in communication with the elemental analyzer is configured to calculate the amount and control the metering of other raw materials required to obtain the desired composition of the calcinated raw material. For example, the programmable control system may determine that the concentration of calcium sulfate dihydrate in the calcinated raw material is too low, calculate the amount of calcium sulfate dihydrate that must be added to the calcinated raw material, and communicate with a control valve to meter the addition of a purified calcium sulfate dihydrate to the calcinated raw material in a mixer to obtain a modified calcinated raw material having the desired chemical composition before it is used in the manufacturing of gypsum board.

Exemplary Example 2

Another exemplary embodiment of a method for analyzing a raw material for the manufacture of gypsum products is illustrated in FIG. 3. A raw material comprising gypsum is provided and is undergoes an elemental analysis before it is calcined. The elemental analyzer is configured to detect and measure the concentration of one or more target chemicals, for example, calcium sulfate dehydrate, in the raw material. The raw material optionally may be sorted based on its composition prior to being calcined.

Similar to the embodiment illustrated in FIG. 2, a programmable control system in communication with the elemental analyzer is configured to calculate the amount and control the metering of other raw materials required to obtain the desired composition of the raw material. For example, the programmable control system may determine that the concentration of calcium sulfate dihydrate in the raw material is too low, calculate the amount of calcium sulfate dihydrate that must be added to the raw material, and communicate with a control valve to meter the addition of a purified calcium sulfate dihydrate to the raw material in a mixer to obtain a modified raw material having the desired chemical composition before it is used in the manufacturing of gypsum board. As illustrated in FIG. 3, the raw material may be calcinated after its elemental analysis and before its modification with other materials in the mixer.

It should be apparent that the foregoing relates only to certain embodiments of the present application and the resultant patent. Numerous changes and modifications may be made herein by one of ordinary skill in the art without departing from the general spirit and scope of the invention as defined by the following claims and the equivalents thereof.

Embodiments of the present disclosure further relate to any one or more of the following paragraphs:

1. A method for analyzing a raw material for manufacturing a plurality of gypsum products, the method comprising:
   analyzing the raw material using an elemental analyzer comprises a prompt gamma neutron activation analysis;
   detecting and/or measuring an amount of one or more target chemicals in the raw material; and
   optimizing the amount of the one or more target chemicals in the raw material to improve consistency and quality of the plurality of gypsum products manufactured from the raw material.
2. The method of paragraph 1, further comprising crushing and/or grinding the raw material prior to analyzing the raw material.
3. The method of paragraph 1, wherein the step of optimizing the amount of the one or more target chemicals in the raw material is upstream of calcinating of the raw material.
4. The method of paragraph 1, wherein the step of analyzing the raw material is downstream of calcinating of the raw material.
5. The method of paragraph 1, wherein the step of optimizing the amount of the one or more target chemicals in the raw material comprises sorting the raw material according to the presence of and/or amount of the one or more target chemicals in the raw material.
6. The method of paragraph 5, wherein the one or more target chemicals comprise calcium sulfate dihydrate.
7. The method of paragraph 5, wherein the one or more target chemicals comprise calcium sulfate hemihydrate.
8. The method of paragraph 5, wherein the one or more target chemicals comprise calcium sulfate.
9. The method of paragraph 1, wherein the elemental analyzer comprises a prompt gamma neutron activation analysis, controlled neutron analysis, x-ray fluorescence, laser spectroscopy or x-ray diffraction.
10. The method of paragraph 1, wherein the elemental analyzer comprises a prompt gamma neutron activation analysis.
11. The method of paragraph 1, wherein the elemental analyzer is configured to detect and/or measure the amount of one or more target chemicals selected from the group consisting of gypsum (calcium sulfate dihydrate), calcium sulfate hemihydrate, calcium sulfate anhydrite, acid solubles, acid insolubles, organics, water, salts, iron, sulfur, and combinations thereof.
12. The method of paragraph 11, wherein the acid solubles comprise limestone.

13. The method of paragraph 11, wherein the acid insolubles comprise, sand, shale, clay, silica phyllosilicates, or combinations thereof.

14. The method of paragraph 11, wherein the step of optimizing the amount of the one or more target chemicals in the raw material comprises mixing the raw material with one or more other materials selected from the group consisting of starch, potash, boric acid, accelerators, foaming agents, retarders, and dispersing agents.

15. The method of paragraph 14, further comprising calcinating the raw material downstream of the step of analyzing the raw material and upstream of mixing the raw material with one or more other materials.

16. The method of paragraph 14, wherein the step of optimizing the amount of the one or more target chemicals in the raw material further comprises sorting the raw material according to the presence of and/or amount of the one or more target chemicals in the raw material downstream of the step of analyzing the raw material and upstream of mixing the raw material with one or more other materials.

17. The method of paragraph 16, wherein the one or more target chemicals are selected from the group consisting of calcium sulfate dihydrate, calcium sulfate hemihydrate, calcium sulfate anhydrite, chloride salts, sulfur, iron, aluminum silicates, calcium carbonate, and combinations thereof.

18. The method of paragraph 1, wherein the method is effective to reduce variability of the elemental chemistry of the gypsum product.

19. A plurality of gypsum products prepared by the method of paragraph 1.

20. A plurality of analyzed gypsum products having improved consistency and quality as characterized by a reduced weight variability, an improved content uniformity, or a combination thereof 21. The plurality of gypsum products of paragraph 20, wherein the reduced weight variability comprises a weight variability of less than about 150 lbs per 1000 ft$^2$.

22. The plurality of gypsum products of paragraph 20, wherein the reduced weight variability comprises a weight variability of less than about 100 lbs per 1000 ft$^2$.

23. The plurality of gypsum products of paragraph 20, wherein the reduced weight variability comprises a weight variability of less than about 50 lbs per 1000 ft$^2$.

24. The plurality of gypsum products of paragraph 20, wherein the reduced weight variability comprises a weight variability of less than about 10 lbs per 1000 ft$^2$.

25. The plurality of gypsum products of paragraph 20, wherein the improved content uniformity is characterized by a calcium sulfate dihydrate concentration variability of less than about ±10%.

26. The plurality of gypsum products of paragraph 20, wherein the improved content uniformity is characterized by a calcium sulfate dihydrate concentration variability of less than about ±5%.

27. The plurality of gypsum products of paragraph 20, wherein the improved content uniformity is characterized by a calcium sulfate dihydrate concentration variability of less than about ±2%.

28. The plurality of gypsum products of paragraph 20, wherein the improved content uniformity is characterized by a calcium sulfate dihydrate concentration variability of less than about ±1%.

29. The plurality of gypsum products of paragraph 20, wherein the gypsum product is selected from the group consisting of a gypsum board, a plaster, or a joint compound.

30. A method for analyzing a plurality of gypsum products, the method comprising:
analyzing the plurality of gypsum products using an elemental analyzer comprising a prompt gamma neutron activation analysis;
detecting and/or measuring the presence and/or amount of one or more target chemicals in the plurality of gypsum products; and
sorting the plurality of gypsum products based on the presence and/or amount or the one or more target chemicals to improve consistency and quality of the plurality of gypsum products.

31. A method for analyzing a raw material for manufacturing a plurality of gypsum products on site at a mine, the method comprising:
analyzing the raw material on site at a mine using an elemental analyzer comprising a prompt gamma neutron activation analysis;
detecting and/or measuring an amount of one or more target chemicals in the raw material; and
sorting the raw material according to the presence of and/or amount of one or more target chemicals in the raw material.

32. A system for analyzing a raw material for manufacturing a plurality of gypsum products, the system comprising:
an elemental analyzer configured to detect and/or measure an amount of one or more target chemicals in the raw material; and
a programmable control system configured to optimize the amount of the one or more target chemicals in the raw material feed.

33. The system of paragraph 32, wherein the elemental analyzer comprises a prompt gamma neutron activation analysis, controlled neutron analysis, x-ray fluorescence, laser spectroscopy or x-ray diffraction.

34. A method according to any one of the embodiments provided herein.

35. A system according to any one of the embodiments provided herein

The invention claimed is:

1. A method for analyzing a raw material for manufacturing a plurality of gypsum products, the method comprising:
analyzing the raw material using an elemental analyzer comprises a prompt gamma neutron activation analysis;
detecting and/or measuring an amount of one or more target chemicals in the raw material; and
optimizing the amount of the one or more target chemicals in the raw material to improve consistency and quality of the plurality of gypsum products manufactured from the raw material,
wherein the one or more target chemicals comprise a material selected from the group consisting of calcium sulfate, calcium sulfate dihydrate, and calcium sulfate hemihydrate.

2. The method of claim 1, further comprising crushing and/or grinding the raw material prior to analyzing the raw material.

3. The method of claim 1, wherein the step of optimizing the amount of the one or more target chemicals in the raw material is upstream of calcinating of the raw material.

4. The method of claim 1, wherein the step of analyzing the raw material is downstream of calcinating of the raw material.

5. The method of claim 1, wherein the step of optimizing the amount of the one or more target chemicals in the raw material comprises sorting the raw material according to the presence of and/or amount of the one or more target chemicals in the raw material.

6. The method of claim 1, wherein the method is effective to reduce variability of the elemental chemistry of the gypsum product.

7. A plurality of gypsum products prepared by the method of claim 1.

8. A method for analyzing a raw material for manufacturing a plurality of gypsum products, the method comprising:
   analyzing the raw material using an elemental analyzer comprises a prompt gamma neutron activation analysis;
   detecting and/or measuring an amount of one or more target chemicals in the raw material; and
   optimizing the amount of the one or more target chemicals in the raw material to improve consistency and quality of the plurality of gypsum products manufactured from the raw material,
   wherein the elemental analyzer is configured to detect and/or measure the amount of one or more target chemicals selected from the group consisting of gypsum (calcium sulfate dihydrate), calcium sulfate hemihydrate, calcium sulfate anhydrite, acid solubles, acid insolubles, organics, water, salts, iron, sulfur, and combinations thereof, and
   wherein the step of optimizing the amount of the one or more target chemicals in the raw material comprises:
      mixing the raw material with one or more other materials selected from the group consisting of starch, potash, boric acid, accelerators, foaming agents, retarders, and dispersing agents, and
      sorting the raw material according to the presence of and/or amount of the one or more target chemicals in the raw material downstream of the step of analyzing the raw material and upstream of mixing the raw material with one or more other materials.

9. The method of claim 8, wherein the acid solubles comprise limestone.

10. The method of claim 8, wherein the acid insolubles comprise, sand, shale, clay, silica phyllosilicates, or combinations thereof.

11. The method of claim 8, further comprising calcinating the raw material downstream of the step of analyzing the raw material and upstream of mixing the raw material with one or more other materials.

12. The method of claim 8, further comprising crushing and/or grinding the raw material prior to analyzing the raw material.

13. The method of claim 8, wherein the method is effective to reduce variability of the elemental chemistry of the gypsum product.

14. A plurality of gypsum products prepared by the method of claim 8.

15. A method for analyzing a plurality of gypsum products, the method comprising:
   analyzing the plurality of gypsum products using an elemental analyzer comprising a prompt gamma neutron activation analysis;
   detecting and/or measuring the presence and/or amount of one or more target chemicals in the plurality of gypsum products; and
   sorting the plurality of gypsum products based on the presence and/or amount or the one or more target chemicals to improve consistency and quality of the plurality of gypsum products,
   wherein the one or more target chemicals comprise a material selected from the group consisting of calcium sulfate, calcium sulfate dihydrate, and calcium sulfate hemihydrate.

16. A method for analyzing a raw material for manufacturing a plurality of gypsum products on site at a mine, the method comprising:
   analyzing the raw material on site at a mine using an elemental analyzer comprising a prompt gamma neutron activation analysis;
   detecting and/or measuring an amount of one or more target chemicals in the raw material; and
   sorting the raw material according to the presence of and/or amount of one or more target chemicals in the raw material,
   wherein the one or more target chemicals comprise a material selected from the group consisting of calcium sulfate, calcium sulfate dihydrate, and calcium sulfate hemihydrate.

17. A system for analyzing a raw material for manufacturing a plurality of gypsum products, the system comprising:
   an elemental analyzer configured to detect and/or measure an amount of one or more target chemicals in the raw material; and
   a programmable control system configured to optimize the amount of the one or more target chemicals in the raw material feed,
   wherein the one or more target chemicals comprise a material selected from the group consisting of calcium sulfate, calcium sulfate dihydrate, and calcium sulfate hemihydrate.

* * * * *